(12) United States Patent
Moreno et al.

(10) Patent No.: US 8,377,481 B2
(45) Date of Patent: Feb. 19, 2013

(54) APPARATUS AND METHOD TO GENERATE A MIXTURE OF HYDROGEN PEROXIDE GAS AND A CARRIER GAS

(76) Inventors: Gil G. Moreno, Tampa, FL (US); Gil Moreno, Tampa, FL (US)

( * ) Notice: Subject to any disclaimer, the term of this patent is extended or adjusted under 35 U.S.C. 154(b) by 131 days.

(21) Appl. No.: 12/590,272

(22) Filed: Nov. 6, 2009

(65) Prior Publication Data

US 2011/0111052 A1    May 12, 2011

(51) Int. Cl.
- *A61K 33/40* (2006.01)
- *A61K 47/00* (2006.01)
- *A61M 37/00* (2006.01)
- *A61M 31/00* (2006.01)
- *A61P 43/00* (2006.01)
- *A61P 31/00* (2006.01)

(52) U.S. Cl. ............ 424/616; 604/24; 604/26; 604/514; 514/771

(58) Field of Classification Search ................... 424/616; 604/24, 26, 514
See application file for complete search history.

(56) References Cited

U.S. PATENT DOCUMENTS

| | | | | |
|---|---|---|---|---|
| 4,550,010 | A | * | 10/1985 | Chelu ............................. 422/4 |
| 7,244,354 | B2 | | 7/2007 | Burris |
| 7,294,320 | B2 | * | 11/2007 | Pettibone ...................... 423/210 |
| 7,347,201 | B2 | | 3/2008 | Djupesland |
| 2008/0071382 | A1 | * | 3/2008 | Kumar et al. .............. 623/23.57 |
| 2008/0314391 | A1 | * | 12/2008 | Acharya ................... 128/207.18 |

\* cited by examiner

*Primary Examiner* — John Pak
*Assistant Examiner* — Nathan W Schlientz
(74) *Attorney, Agent, or Firm* — Frijouf, Rust & Pyle, P.A.

(57) ABSTRACT

This relates to a method to generate a mixture of Hydrogen Peroxide gas and a Carrier gas, consisting in passing a dry Carrier gas through a solution of Hydrogen Peroxide.

15 Claims, 1 Drawing Sheet

APPARATUS AND METHOD TO GENERATE A MIXTURE OF HYDROGEN PEROXIDE GAS AND A CARRIER GAS

BACKGROUND OF THE INVENTION

Hydrogen Peroxide liquid has been used for long time as an effective means to destroy undesirable microorganisms on humans and living creatures. The nasal and vocal cavities are a paradise for said microorganisms.

Hydrogen Peroxide is a liquid at normal temperature and barometric pressure. Its boiling point is 150.2 grades centigrade, and is miscible with water. The present invention delivers a mixture of hydrogen peroxide gas and a carrier gas to nose, mouth and ears. As a gas the hydrogen peroxide diffuses and is capable of traveling to the most difficult locations.

The applicants set up tests to determine the efficiency of the present invention. A dry carrier gas was passed thru a cell containing a solution of 3 per cent Hydrogen Peroxide available in the drug stores. The cell output was far from the solution surface to allow only a mixture of carrier gas and hydrogen peroxide gas to be delivered to a solution of Potassium Permanganate, which normally is pink, turning it yellow that indicated the carrier gas contained Hydrogen Peroxide gas. The tests were performed at 90 and 70 per cent relative humidity and the carrier gas was dry air but other dry carrier gases may be used.

During a hard breath-hold, the epiglottis closes the access to the lungs. Then the nose, mouth and ears can be irrigated with Hydrogen Peroxide rich gas. After irrigation the air in the lungs is expelled thru the nose and mouth to remove the Hydrogen Peroxide rich gas. Some Hydrogen Peroxide remains trapped in the mucus for a short period extending the germ killer action.

At present there is not a simple and practical method to irrigate the nose, mouth and ears with Hydrogen Peroxide rich gas.

U.S. Pat. No. 7,347,201 is complicated and would require extensive modifications to accomplish delivery of Hydrogen Peroxide gas.

U.S. Pat. No. 7,244,354 is extremely complicated and uses ozone dissolved in water or solution.

The present invention provides an economical and easy way to destroy the majority of harmful microorganisms infesting the nose, mouth and ears.

SUMMARY OF THE INVENTION

The principal object of the present invention is to provide a method to irrigate the nose, mouth and ears with Hydrogen Peroxide rich gas that is simple, is portable and requires minimum mental effort to operate.

It is also an object of the present invention to provide a method, which is inexpensive.

Another object of the present invention is to provide a method that is attractive and pleasant to use.

A further object is to provide a method that will contribute to a healthy life.

For accomplishing these objects a Hydrogen Peroxide rich gas is pumped into the nose, mouse or ears using a nozzle.

DESCRIPTION OF THE PREFERRED EMBODIMENTS

Figure 1:
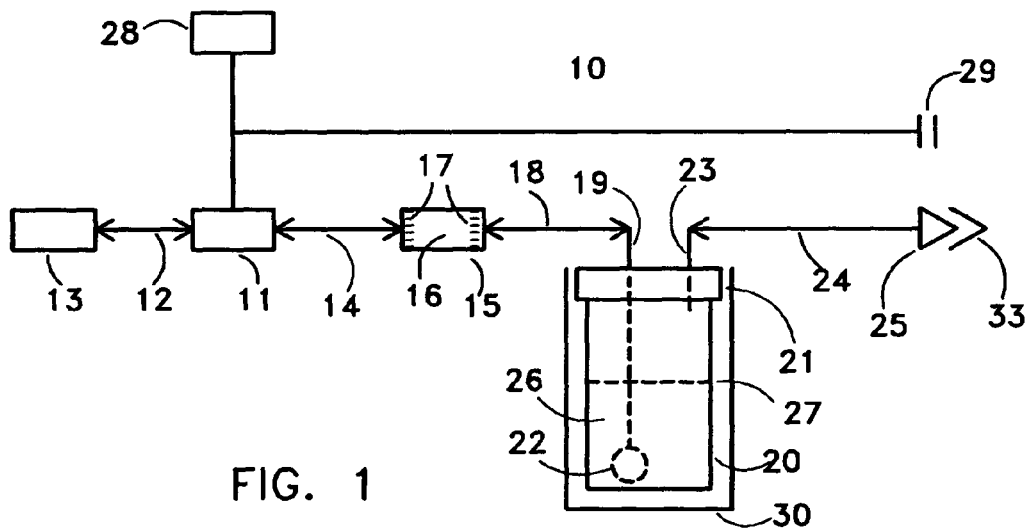
FIG. 1 shows the most relevant components of the device to irrigate the nose, mouth and ears with Hydrogen Peroxide rich gas.

Referring to FIG. 1 the device generally designated 10 comprises a carrier gas pump 11 connected with hose 12 to a gas filter 13. Said carrier gas pump 11 is also connected with hose 14 to carrier gas dryer cell 15 containing silica gel desiccant or equivalent 16. Said 15 has at entrance and exit wire mesh 17 to prevent escape of 16. Said 15 is connected with hose 18 to a first tube 19 of bubbling cell 20 made of translucent material. Said 19 penetrates lid 21 of 20 and has at the end an air stone 22 close to the bottom of said 20. One end of a second tube 23 is just long enough to penetrate said lid 21. The other end of 23 is connected to one end of hose 24, and the other end of 24 is connected to delivery nozzle 25 or 35. Cap 33 fits tight 25 and 35 to prevent access of dust and insects during storage. Said 20 is filled with solution 26 of hydrogen peroxide up to indicating mark 27 to allow only a mixture of hydrogen peroxide gas and carrier gas to exit thru said 24. Electric power 28 from batteries or utility service feeds said 11 via momentary normally open push button switch 29. Light shield 30 covers said 20 and can be removed during refilling to make visible said 27.

Figure 2:
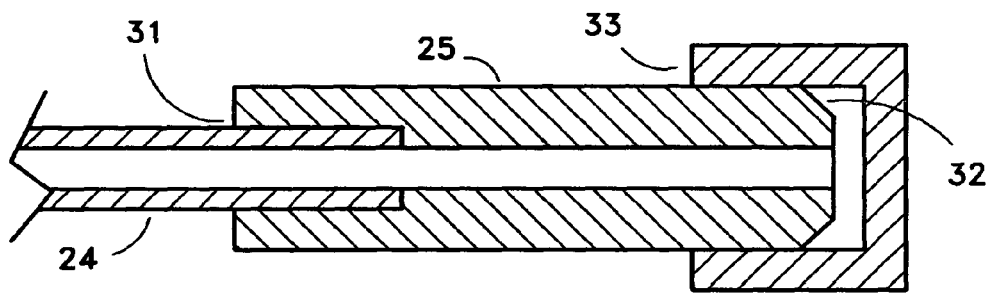
FIG. 2 is a cross sectional view of the Hydrogen Peroxide rich gas delivery nozzle with a cylindrical cavity to accept the feeding hose, and protective cap.

Referring to FIG. 2 nozzle 25 is of sufficient length and diameter to be held by fingers. One end of said 25 has a cylindrical cavity 31 to accept tight hose 24. The other end 32 of said 25 is conical to facilitate alignment, of diameter large enough to prevent penetration in human nostril and ears. A cap 33 fits tight to 25 to prevent access of dust and insects during storage.

Figure 3:
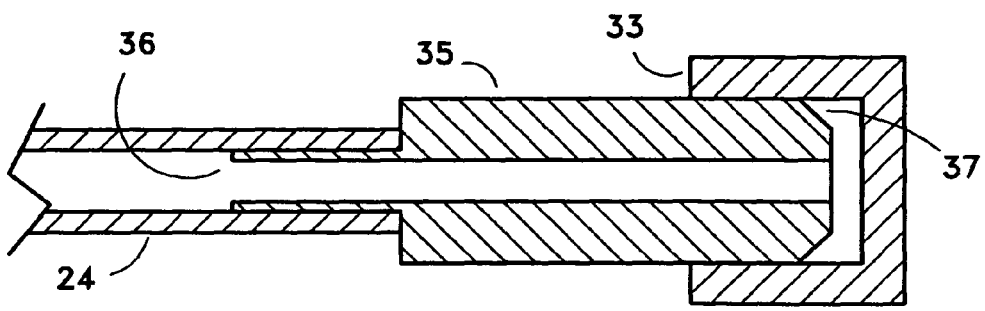
FIG. 3 is a cross sectional view of the Hydrogen Peroxide rich gas delivery nozzle with a cylindrical extension to fit inside the feeding hose, and protective cap.

Referring to FIG. 3 nozzle 35 is of sufficient length and diameter to be held by fingers. One end of said 35 has a cylindrical extension 36 to penetrate tight hose 24. The other end 37 of said 35 is conical to facilitate alignment, of diameter large enough to prevent penetration in human nostril and ears. A cap 33 fits tight to 35 to prevent access of dust and insects during storage.

Although the invention has been disclosed in its prefer forms with a certain degree of particularity, it is understood that the invention of the preferred forms has been made by way of examples, that numerous changes in the detail of construction and the combination and arrangement of parts may be resorted to without departing from the spirit and scope of the invention.

What is claimed is:

1. An undesirable microorganism treatment device for dispensing a gas into a nose, a mouth and/or an ear of a living creature, comprising:
    a cell containing a solution of hydrogen peroxide;
    a lid engaging said cell for sealing said solution of hydrogen peroxide within said cell;
    a first tube penetrating said lid and extending into said solution of hydrogen peroxide;
    a second tube penetrating said lid and positioned above said solution of hydrogen peroxide;
    a carrier gas pump for propelling a carrier gas;
    an input hose coupling said carrier gas pump with said first tube for positioning said carrier gas within said solution of hydrogen peroxide;

a nozzle for dispensing into the nose, the mouth and/or the ear;

an output hose coupling said second tube and said nozzle for conveying a mixture of a hydrogen peroxide gas and said carrier gas from said cell to the nose, the mouth and/or the ear; and said hydrogen peroxide gas irrigating and diffusing within the nose, the mouth and/or the ear for destroying undesirable microorganisms.

2. An undesirable microorganism treatment device for dispensing a gas into a nose, a mouth and/or an ear of a living creature, comprising:

a cell containing a solution of hydrogen peroxide;

an indicating mark defined by the level of said solution of hydrogen peroxide within said cell;

a lid engaging said cell for sealing said solution of hydrogen peroxide within said cell;

a first tube penetrating said lid and extending below said indicating mark;

a second tube penetrating said lid and positioned above said indicating mark;

a carrier gas pump for propelling a carrier gas;

an input hose coupling said carrier gas pump with said first tube for positioning said carrier gas within said solution of hydrogen peroxide;

a nozzle for dispensing into the nose, the mouth and/or the ear;

an output hose coupling said second tube and said nozzle for conveying a mixture of a hydrogen peroxide gas and said carrier gas from said cell to the nose, the mouth and/or the ear; and said hydrogen peroxide gas irrigating and diffusing within the nose, the mouth and/or the ear for destroying undesirable microorganisms.

3. An undesirable microorganism treatment device as set forth in claim 2, wherein said solution of hydrogen peroxide has a concentration of 3%.

4. An undesirable microorganism treatment device as set forth in claim 2, wherein said carrier gas is dry air.

5. An undesirable microorganism treatment device as set forth in claim 2, further including an air stone coupled to said first tube for dispersing said carrier gas within said solution of hydrogen peroxide.

6. An undesirable microorganism treatment device as set forth in claim 2, further including a carrier gas dryer cell in line with said input hose; and a moisture absorption substance positioned within said carrier gas dryer cell for serving as a desiccant.

7. An undesirable microorganism treatment device as set forth in claim 2, further including a carrier gas dryer cell in line with said input hose;

a moisture absorption substance positioned within said carrier gas dryer cell for serving as a desiccant; and said moisture absorption substance including a silica gel.

8. An undesirable microorganism treatment device as set forth in claim 2, further including a light shield covering said cell for reducing the rate of decomposition of said solution of hydrogen peroxide.

9. An undesirable microorganism treatment device as set forth in claim 3, wherein said cell includes a translucent material for viewing said indicating mark during refilling of said cell with said solution of hydrogen peroxide; and a light shield covering said cell for reducing the rate of decomposition of said hydrogen peroxide.

10. An undesirable microorganism treatment device as set forth in claim 2, further including a cap engaging said nozzle for preventing debris from entering said nozzle during storage.

11. A method for treating an undesirable microorganism within a nose, a mouth and/or an ear of a living creature, the method comprising the steps of:

absorbing moisture in a carrier gas within a carrier gas dryer cell;

inputting the carrier gas into a solution of hydrogen peroxide within a cell;

outputting a mixture of a hydrogen peroxide gas and the carrier gas from the cell to a nozzle;

dispensing the mixture of the hydrogen peroxide gas and the carrier gas from the nozzle and into the nose, the mouth and/or the ear;

irrigating and diffusing by the hydrogen peroxide gas within the nose, the mouth and/or the ear; and destroying undesirable microorganisms by the contact between the undesirable microorganisms and the hydrogen peroxide gas.

12. A method for treating an undesirable microorganism as set forth in claim 11, wherein the step of outputting the mixture of the hydrogen peroxide gas and the carrier gas from the cell to the nozzle further comprises the steps of:

inhaling by the living creature; and holding the breath by the living creature for closing the epiglottis.

13. A method for treating an undesirable microorganism as set forth in claim 11, wherein the step of destroying undesirable microorganisms by the contact between the undesirable microorganisms and the hydrogen peroxide gas further comprising the step of exhaling by the living creature for expelling the hydrogen peroxide gas from the nose and the mouth.

14. A method for treating an undesirable microorganism as set forth in claim 11, wherein the step of destroying undesirable microorganisms by the contact between the undesirable microorganisms and the hydrogen peroxide gas further comprising the steps of:

exhaling by the living creature for expelling a portion of the hydrogen peroxide gas from the nose and the mouth; and retaining a portion of the hydrogen peroxide gas within the nose and the mouth for increasing the destroying of undesirable microorganisms.

15. A method for treating an undesirable microorganism within a nose, a mouth and/or an ear of a living creature, the method comprising the steps of:

propelling a carrier gas through a carrier gas pump;

inputting the carrier gas into a solution of hydrogen peroxide within a cell;

outputting a mixture of a hydrogen peroxide gas and said carrier gas from said cell to a nozzle;

dispensing said mixture of said hydrogen peroxide gas and said carrier gas from said nozzle and into the nose, the mouth and/or the ear;

irrigating and diffusing by said hydrogen peroxide gas within the nose, the mouth and/or the ear; and destroying undesirable microorganisms by the contact between the undesirable microorganisms and said hydrogen peroxide gas.

* * * * *